United States Patent
Cabrera et al.

(10) Patent No.: US 11,730,481 B2
(45) Date of Patent: Aug. 22, 2023

(54) ASSEMBLIES FOR RETAINING A TROCAR ASSEMBLY

(71) Applicant: Covidien LP, Mansfield, MA (US)

(72) Inventors: Ramiro D. Cabrera, Cheshire, CT (US); Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 237 days.

(21) Appl. No.: 17/109,718

(22) Filed: Dec. 2, 2020

(65) Prior Publication Data

US 2021/0204950 A1 Jul. 8, 2021

Related U.S. Application Data

(60) Provisional application No. 62/957,380, filed on Jan. 6, 2020.

(51) Int. Cl.
*A61B 17/34* (2006.01)
*A61B 17/115* (2006.01)
*A61B 17/11* (2006.01)

(52) U.S. Cl.
CPC ...... *A61B 17/1155* (2013.01); *A61B 17/3417* (2013.01); *A61B 2017/1132* (2013.01)

(58) Field of Classification Search
None
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated May 17, 2021 issued in corresponding EP Appln. No. 21150249.7.

(Continued)

*Primary Examiner* — Chinyere J Rushing-Tucker
(74) *Attorney, Agent, or Firm* — Carter, DeLuca & Farrell LLP

(57) ABSTRACT

A trocar retaining assembly is configured to releasably retain a trocar assembly and includes a housing assembly and a linkage assembly. A first arm is engaged with a first lateral linkage of the linkage assembly, and a portion of the first arm is slidable between a first position and a second position within a first lateral aperture of the housing assembly. A second arm is engaged with a second lateral aperture of the linkage assembly, and a portion of the second arm is slidable between a first position and a second position within a second lateral aperture of the housing assembly. The trocar assembly is hindered from translating longitudinally relative to the housing assembly when the first arm is in its first position, and the trocar assembly is longitudinally translatable when the first arm is in its second position.

20 Claims, 13 Drawing Sheets

(56) References Cited

U.S. PATENT DOCUMENTS

| | | |
|---|---|---|
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |

(56) References Cited

U.S. PATENT DOCUMENTS

| | | |
|---|---|---|
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | |
|---|---|---|
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,806,973 B2 | 8/2014 | Ross et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |

(56) References Cited

U.S. PATENT DOCUMENTS

| | | | |
|---|---|---|---|
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2016/0143641 A1 | 5/2016 | Sapienza et al. |
| 2016/0157856 A1 | 6/2016 | Williams et al. |
| 2016/0302792 A1 | 10/2016 | Motai |
| 2016/0361057 A1* | 12/2016 | Williams ............. A61B 17/068 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3103402 A1 | 12/2016 |
| EP | 3146905 A1 | 3/2017 |
| EP | 3245959 A2 | 11/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2008107918 A1 | 9/2008 |

OTHER PUBLICATIONS

Extended European Search Report from Appl. No. 14181908.6 dated May 26, 2015.

European Examination Report from Appl. No. 14181908.6 dated May 3, 2016.

* cited by examiner

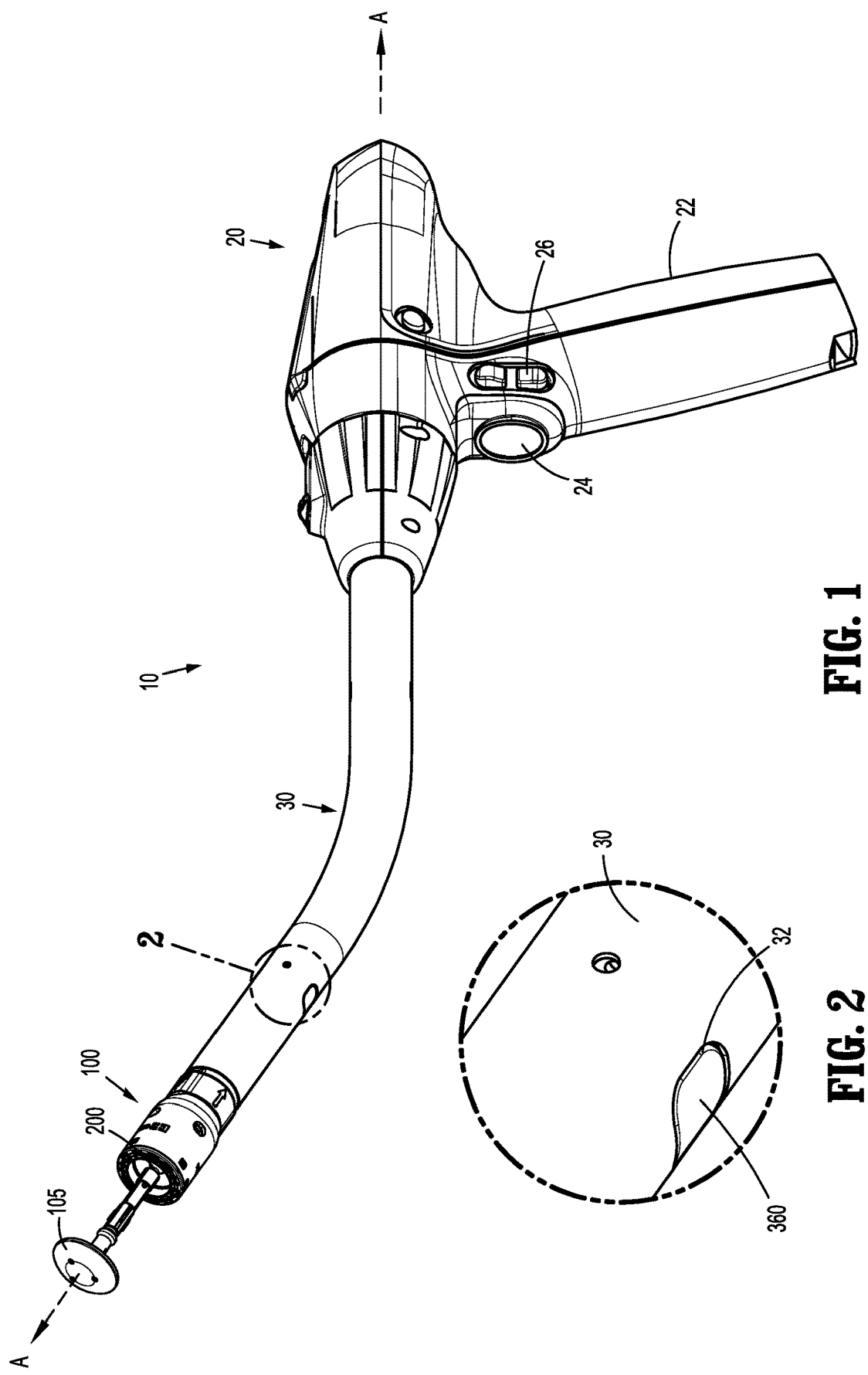

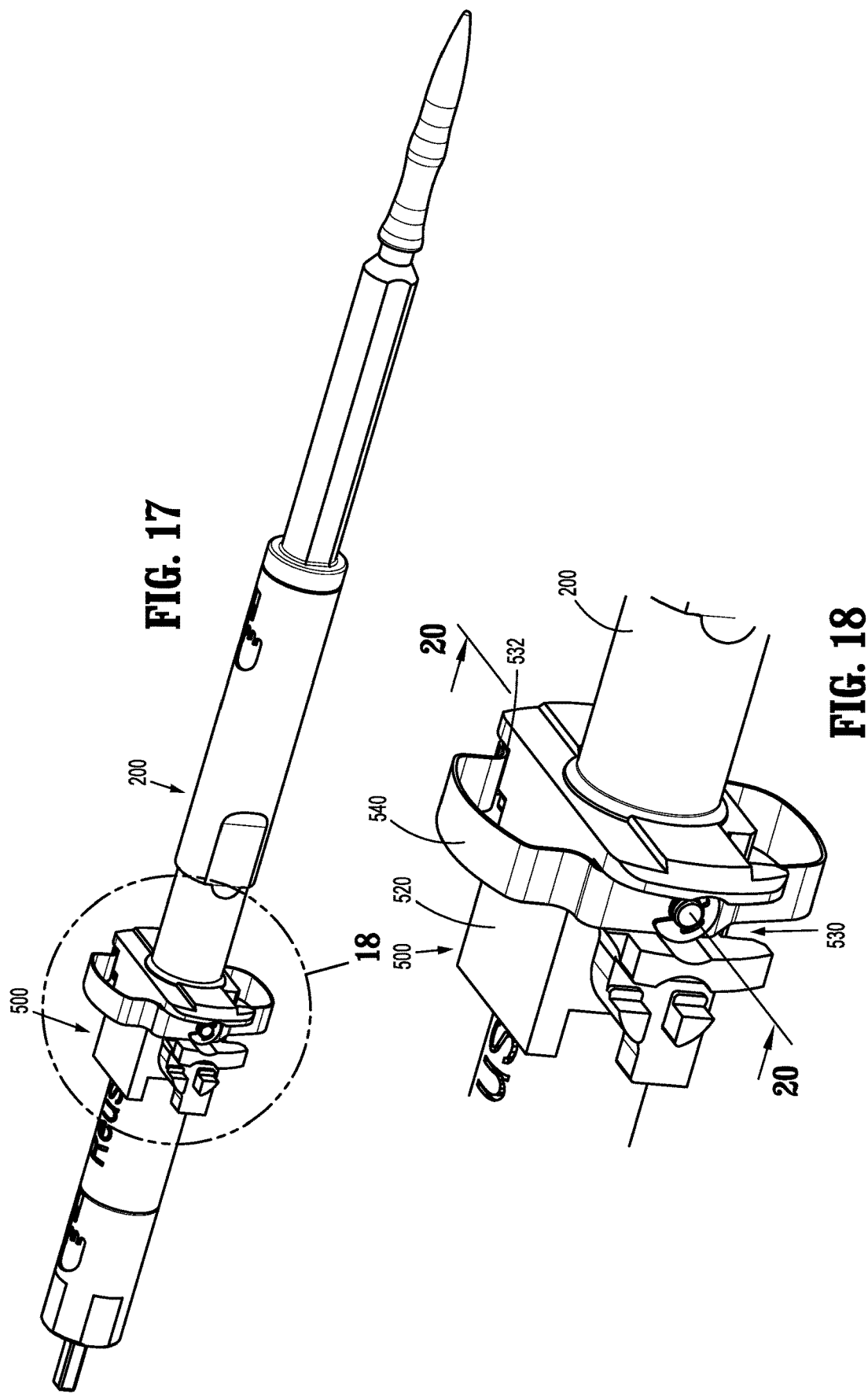

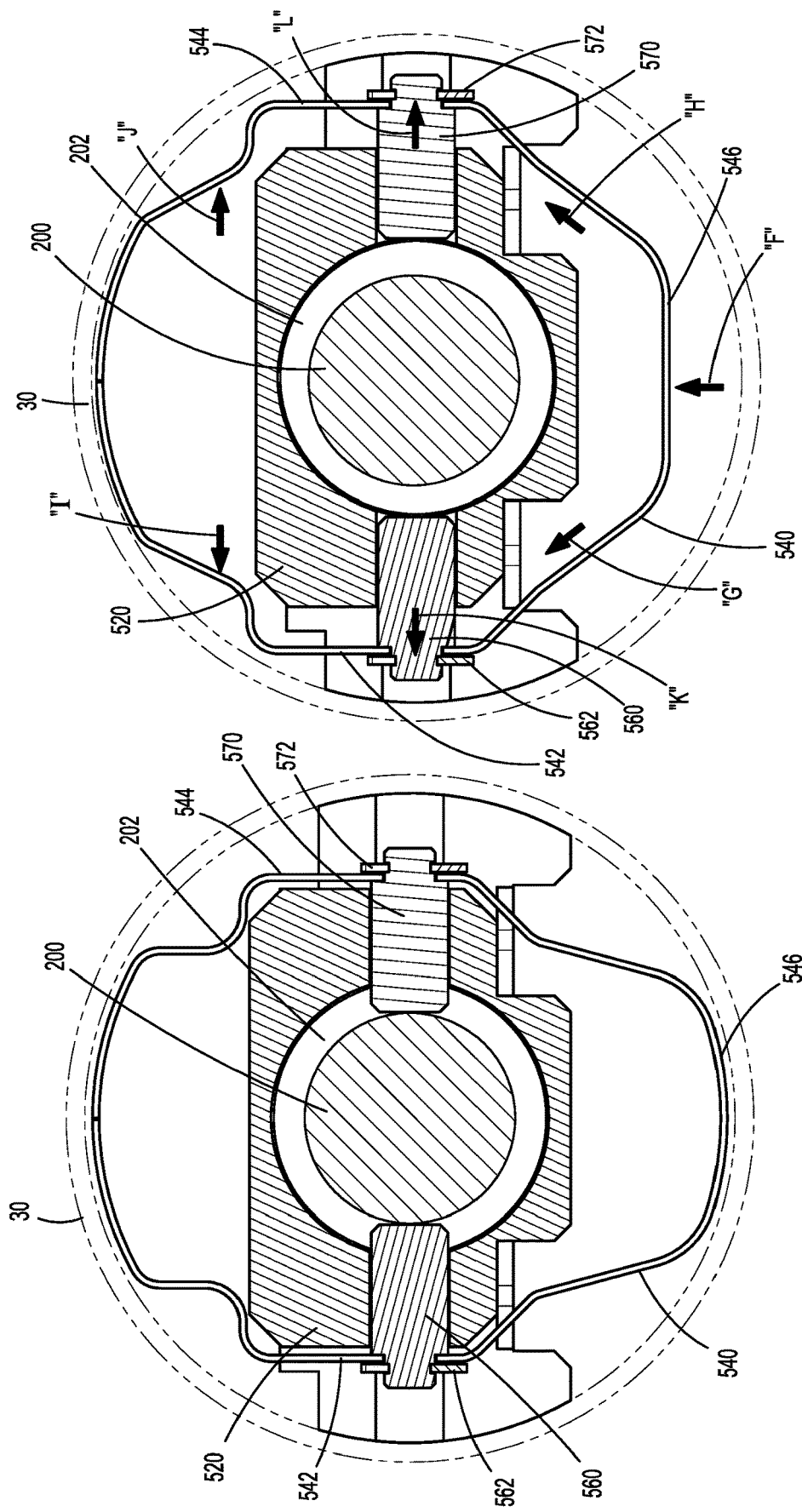

ASSEMBLIES FOR RETAINING A TROCAR ASSEMBLY

CROSS-REFERENCE TO RELATED APPLICATION

The present application claims the benefit of and priority to U.S. Provisional Patent Application Ser. No. 62/957,380, filed on Jan. 6, 2020, the entire disclosure of which is incorporated by reference herein.

BACKGROUND

Technical Field

The present disclosure relates generally to assemblies for retaining a trocar assembly of a surgical stapling instrument. More particularly, the present disclosure relates to assemblies for releasably retaining a trocar assembly partially within an elongated body portion of a surgical stapling instrument.

Background of Related Art

Anastomosis is the surgical joining of separate hollow organ sections. Typically, an anastomosis procedure follows surgery in which a diseased or defective section of hollow tissue is removed, and the end sections are stapled via a surgical stapler. Depending on the desired anastomosis procedure, the end sections may be joined by circular or side-to-side organ reconstruction methods, for instance.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Typically, these instruments include an elongated body portion having a handle portion at a proximal end to actuate the instrument and a staple holding component disposed at a distal end. An anvil assembly including an anvil retention rod with an attached anvil head is mounted to a trocar assembly at the distal end of the instrument adjacent the staple-holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a circular stapling device for hemorrhoid treatment, the anvil head and the staple holding-component of the surgical stapling instrument are inserted through the anus and into the rectum with the anvil head and the staple-holding component in an open or unapproximated position. Thereafter, a pursestring suture is used to pull the internal hemorrhoidal tissue towards the anvil rod. Next, the anvil head and staple-holding component are approximated to clamp the hemorrhoidal tissue between the anvil head and the staple holding component. During the approximation of the anvil head and the staple-holding component, the trocar assembly engages the anvil retention rod. The surgical stapling instrument is fired to remove the hemorrhoidal tissue and staple the cut tissue.

It may be desirable to select a particular trocar assembly depending on the type of surgical procedure being performed. Further, it may be helpful to remove the trocar assembly after use to facilitate the sanitization thereof, if reusing the trocar assembly is desired, for instance.

SUMMARY

The present disclosure relates to a trocar retaining assembly configured to releasably retain a trocar assembly relative to an elongated body portion of a surgical stapling instrument. The trocar retaining assembly includes a housing assembly and a linkage assembly. The housing assembly defines a first lateral aperture, a second lateral aperture, and a trocar aperture. The trocar aperture defines a longitudinal axis and is configured to slidingly receive a portion of a trocar assembly therethrough. The linkage assembly includes a first lateral linkage, a second lateral linkage, a first arm, and a second arm. The first arm is engaged with the first lateral linkage, and a portion of the first arm is slidable between a first position and a second position within the first lateral aperture of the housing assembly. The second arm is engaged with the second lateral aperture, and a portion of the second arm is slidable between a first position and a second position within the second lateral aperture of the housing assembly. The trocar assembly is hindered from translating longitudinally relative to the housing assembly when the first arm is in its first position, and the trocar assembly is longitudinally translatable relative to the housing assembly when the first arm is in its second position.

It is further disclosed that the first arm and the second arm may be biased toward their first positions.

In disclosed embodiments, the linkage assembly may include a lower linkage engaged with the first lateral linkage and the second lateral linkage. In embodiments, moving the lower linkage toward the trocar aperture may cause the first arm to move toward its second position. It is also disclosed that moving the lower linkage toward the trocar aperture may cause the second arm to move toward its second position.

Additionally, it is disclosed that the first lateral linkage may be pivotably connected to the first arm.

In embodiments, the lower linkage may be pivotably connected to the first lateral linkage and the second lateral linkage.

It is further disclosed that the first arm and the second arm may be biased toward the longitudinal axis.

In disclosed embodiments, the first lateral linkage may be pivotably connected to the first arm, the second lateral hinge may be pivotably connected to the second arm, the lower linkage may be pivotably connected to the first lateral linkage and the second lateral linkage, and the first arm and the second arm may be biased toward their first positions.

The present disclosure also relates to a trocar retaining assembly configured to releasably retain a trocar assembly relative to an elongated body portion of a surgical stapling instrument. The trocar retaining assembly includes a housing assembly and a button assembly. The housing assembly defines a trocar aperture which defines a longitudinal axis and is configured to slidingly receive a portion of a trocar assembly therethrough. The button assembly includes a first leg extending from a backspan. A portion of the first leg includes a first curved part defining a first arc length and a second curved part defining a second arc length. The first leg is movable relative to the housing assembly between a first position where the first curved part is coaxial with the longitudinal axis, and a second position where the second curved part is coaxial with the longitudinal axis. The trocar assembly is hindered from translating longitudinally relative to the housing assembly when the first leg is in its second position, and the trocar assembly is longitudinally translatable relative to the housing assembly when the first leg is in its first position.

In disclosed embodiments, the button assembly may include a second leg extending from the backspan. A portion of the second leg may include a first curved part defining the first arc length and a second curved part defining the second arc length. The second leg may be movable relative to the housing assembly between a first position where the first curved part is coaxial with the longitudinal axis, and a second position where the second curved part is coaxial with the longitudinal axis.

It is further disclosed that the first leg may be biased toward its second position.

In embodiments, moving the backspan toward the trocar aperture may cause the first leg to move toward its first position.

It is also disclosed that the housing assembly may define a first cavity disposed on a first lateral side of the trocar aperture, and a second cavity disposed on a second lateral side of the trocar aperture. Additionally, a first biasing member may be disposed at least partially within the first cavity and in contact with the first leg of the button assembly, and a second biasing member may be disposed at least partially within the second cavity and in contact with the second leg of the button assembly.

DESCRIPTION OF THE DRAWINGS

Embodiments of a surgical stapling instrument are disclosed herein with reference to the drawings, wherein:

FIG. 1 is a perspective view of a surgical stapling instrument according to embodiments of the present disclosure;

FIG. 2 is an enlarged view of the area of detail indicated in FIG. 1 illustrating a trocar release actuator;

FIG. 17 is a perspective view of a third embodiment of a trocar retaining assembly engaged with a trocar assembly in accordance with an embodiment of the present disclosure;

FIG. 18 is an enlarged view of the area of detail indicated in FIG. 17;

FIG. 20 is a cross-sectional view of the trocar retaining assembly and the trocar assembly taken along line 20-20 in FIG. 18, and illustrating a trocar release button in a rest position; and FIG. 21 is a cross-sectional view of the trocar retaining assembly and the trocar assembly taken along line 20-20 in FIG. 18, and illustrating the trocar release button in a depressed position.

DETAILED DESCRIPTION

Figure 3:
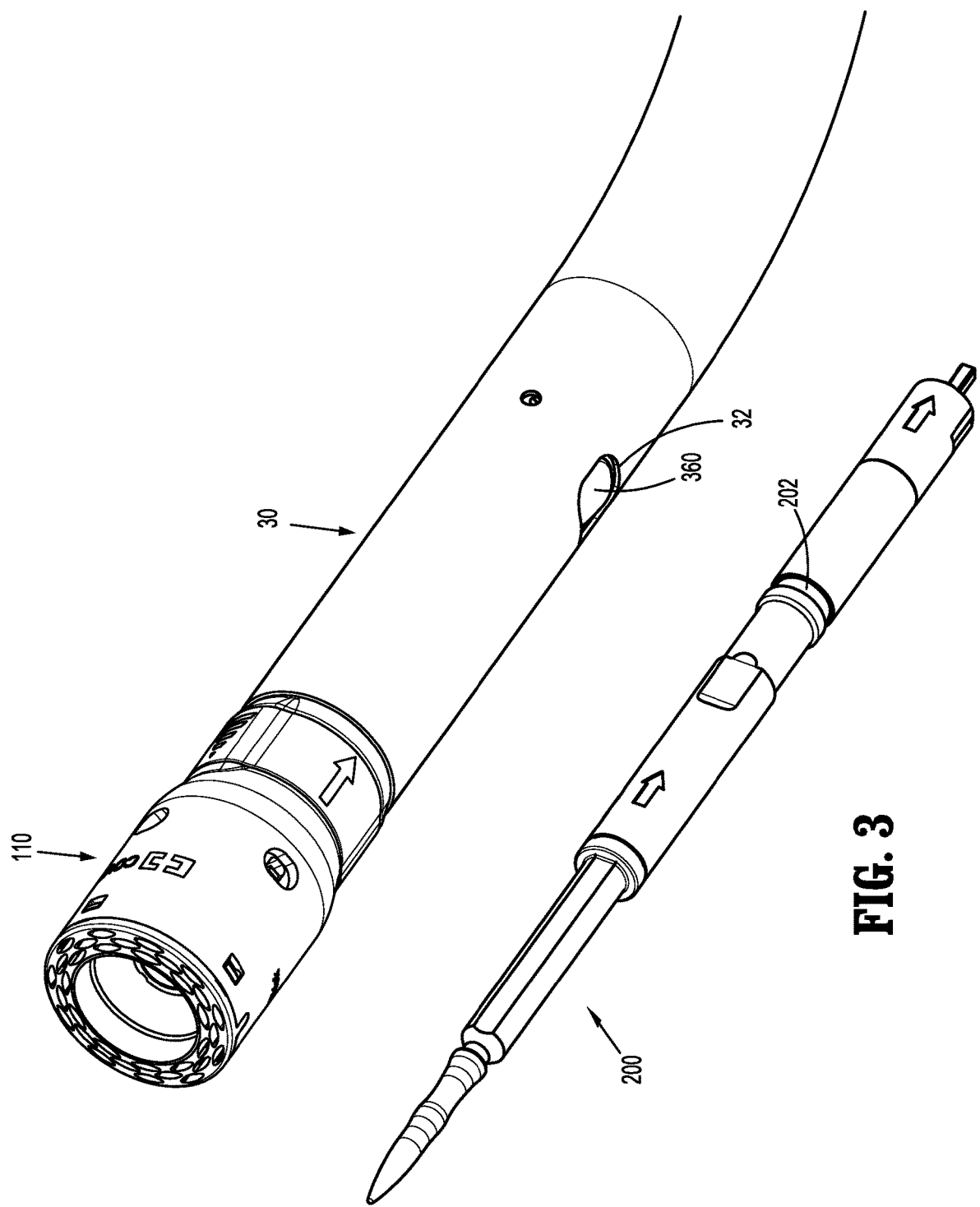
FIG. 3 is an exploded perspective view of an elongated body portion and a trocar assembly of the surgical stapling instrument of FIG. 1.
Figure 4:
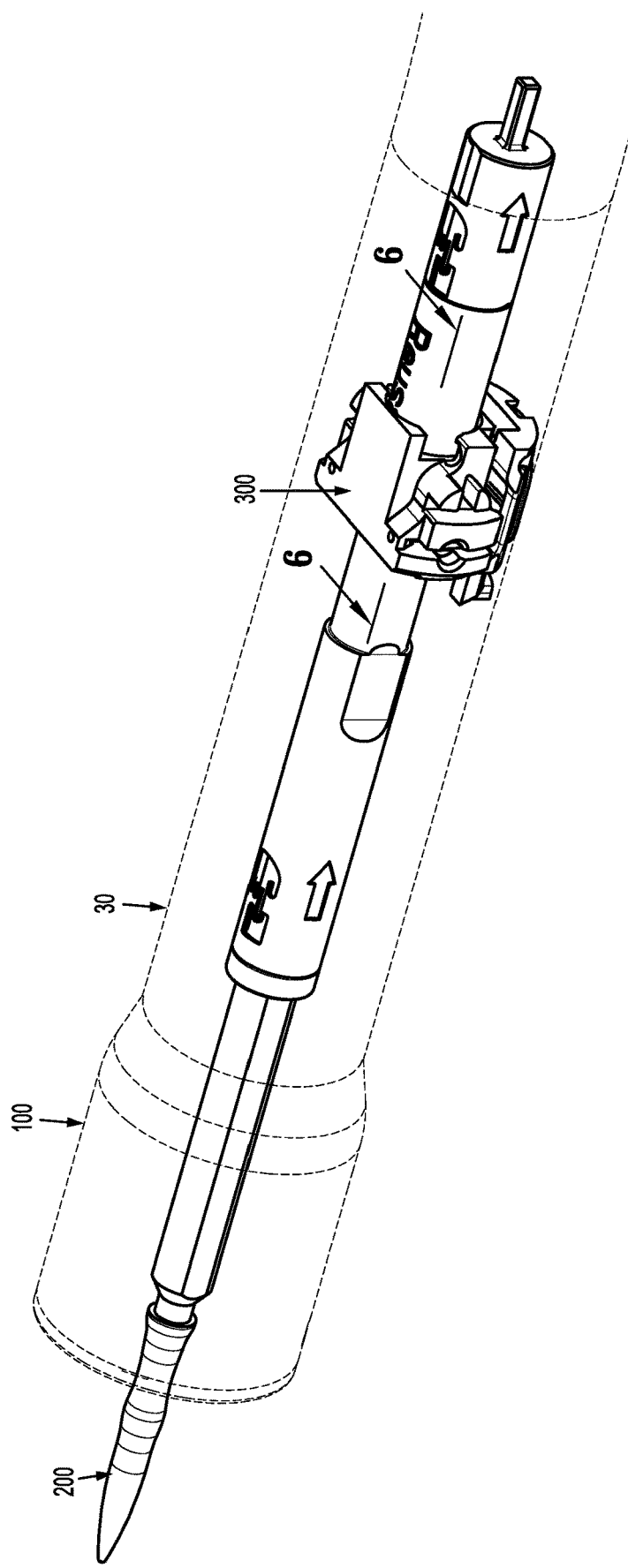
FIG. 4 is a perspective view of a the trocar assembly engaged with the elongated body portion of FIG. 3 including a first embodiment of a trocar retaining assembly.

Embodiments of the presently disclosed trocar retaining assembly of a surgical stapling instrument will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

FIGS. 1 and 2 illustrate an embodiment of a surgical stapling instrument according to the present disclosure, referenced generally as circular stapler 10. While a circular stapler is shown, the various trocar retaining assemblies discussed below are usable with other types of surgical instruments. Circular stapler 10 includes a handle assembly 20, an elongated body portion 30 extending distally from handle assembly 20 and defining a longitudinal axis A-A (e.g., a curved axis), and a shell assembly 100 mounted adjacent a distal end of elongated body portion 30. Handle assembly 20 includes a fixed handle 22 and an actuator 24 (e.g., a push button) (shown) or a trigger (not shown). Handle assembly 20 also includes an approximation mechanism 26 for moving a trocar assembly 200 and an anvil assembly 105 relative to a cartridge assembly 110 of shell assembly 100. The structure and function of handle assembly 20 will only be described herein to the extent necessary. It is envisioned that shell assembly 100 may be used with any actuation assembly, powered or manual, and capable of two independent actuation strokes, for example. Commonly owned U.S. Pat. No. 8,806,973, the content of which is incorporated by reference herein in its entirety, discloses a surgical device having a powered actuator assembly including first and second drive members. In addition, it is envisioned that the independent actuation strokes may be completed by the same drive member completing two strokes or by two separate drive members.

With reference to FIG. 3, cartridge assembly 110, part of elongated body portion 30, and trocar assembly 200 are shown. Trocar assembly 200 is removably secured at least partially within elongated body portion 30 such that trocar assembly 200 may be removed, sanitized, and/or replaced allowing reuse of trocar assembly 200.

Referring now to FIGS. 4-9, a first embodiment of a trocar retaining assembly 300 is shown. Trocar retaining assembly 300 is configured to releasably retain trocar assembly 200 at least partially within elongated body portion 30 of circular stapler 10, and to allow trocar assembly 200 to be removed from elongated body portion 30 for cleaning and/or reuse, for example. Trocar retaining assembly 300 includes a housing assembly 320, a linkage assembly 340, and an actuator 360.

Figure 5:
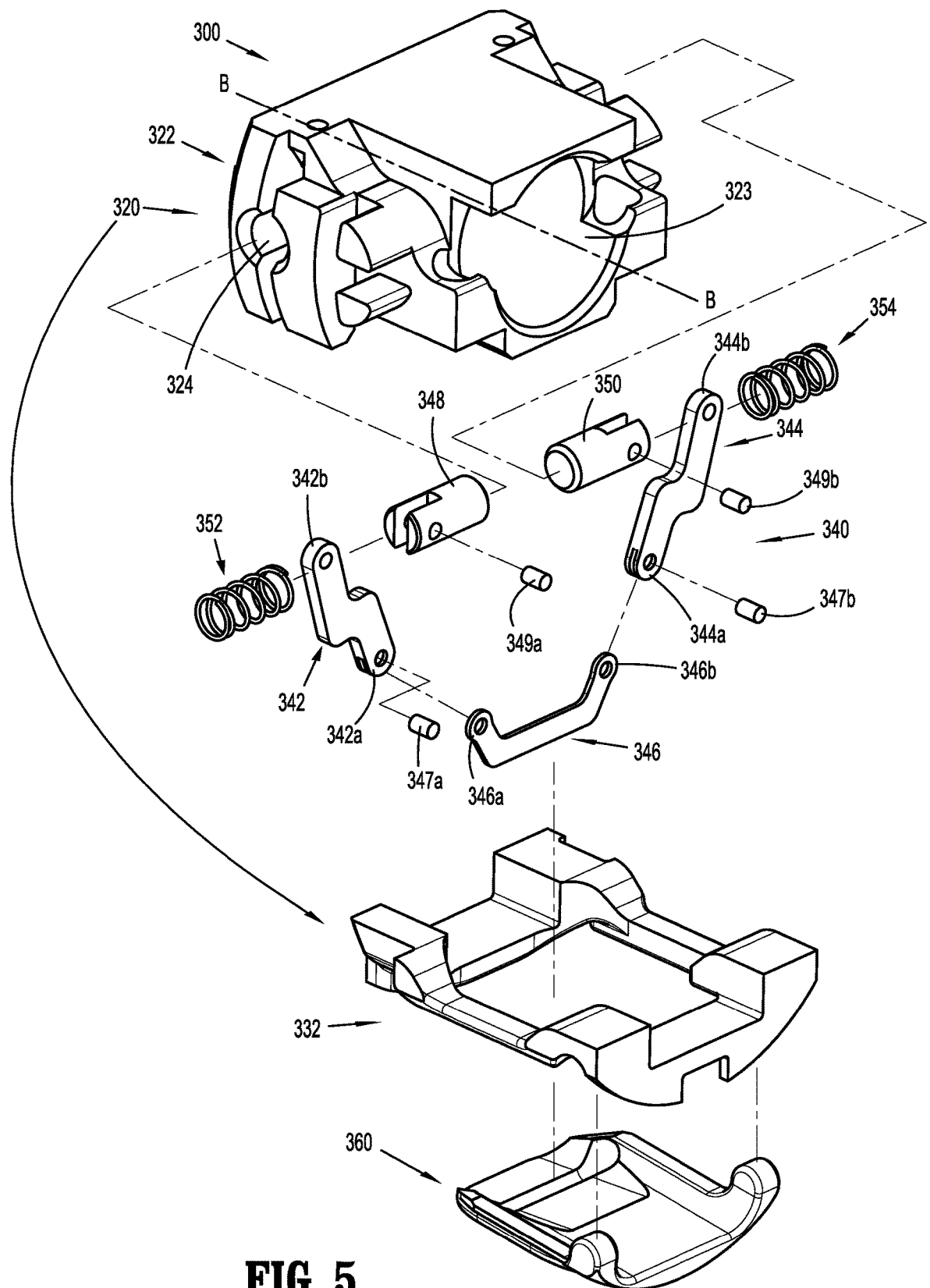
FIG. 5 is an exploded perspective view of the trocar retaining assembly of FIG. 4.
Figure 6:
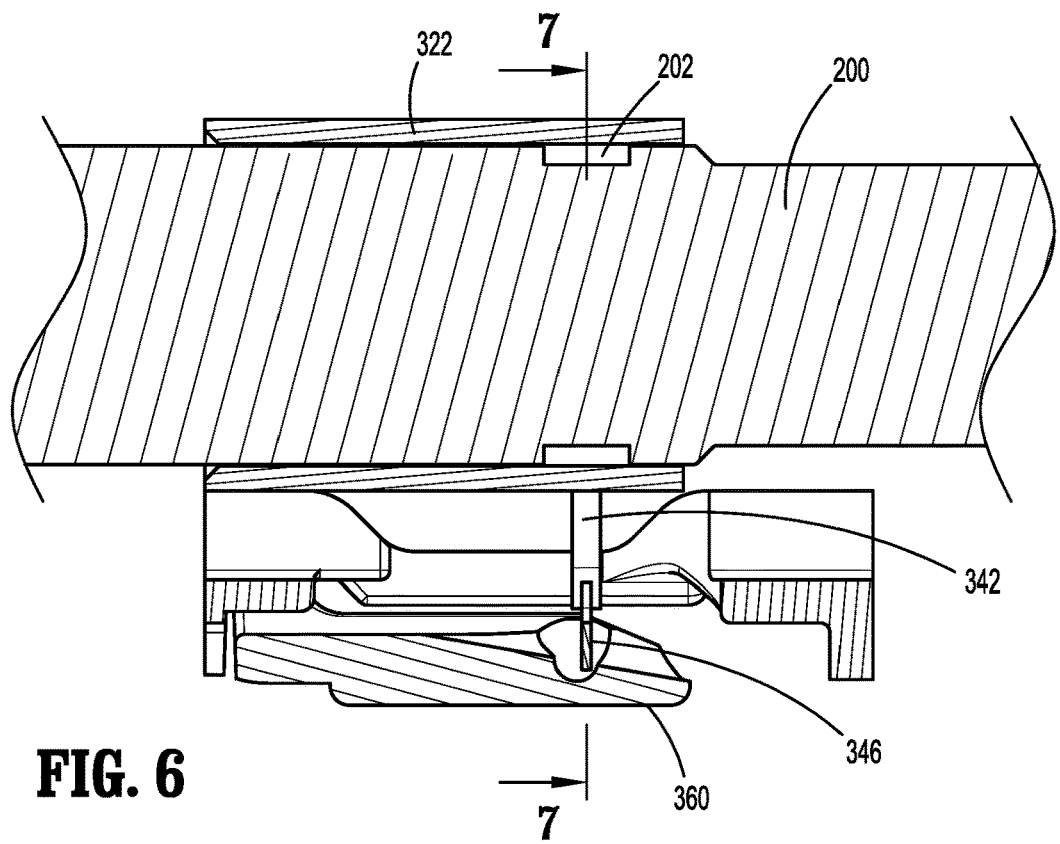
FIG. 6 is a cross-sectional view of the trocar retaining assembly and the trocar assembly taken along line 6-6 in FIG. 4, and illustrating a trocar release button in a rest position.

With particular reference to FIG. 5, housing assembly 320 includes an upper housing 322 and a lower housing 332. Upper housing 322 and lower housing 332 are configured to engage each other in a snap-fit manner, for example. Upper housing 322 defines a trocar aperture 323, which defines a longitudinal axis B-B and which is configured to slidingly receive a portion of trocar assembly 200 therethrough (FIGS. 6-9). The engagement between upper housing 322 and lower housing 332 secures portions of linkage assembly 340 therebetween.

With continued reference to FIG. 5, linkage assembly 340 includes a first lateral linkage 342, a second lateral linkage 344, a lower linkage 346, a first arm 348, a second arm 350, a first biasing member 352 and a second biasing member 354. A lower or first portion 342a of first lateral linkage 342 is pinned to a first lateral portion 346a of lower linkage 346 via a first pin 347a, and an upper or second portion 342b of first lateral linkage 342 is pinned to first arm 348 via a second pin 349a. Additionally, a lower or first portion 344a of second lateral linkage 344 is pinned to a second lateral portion 346b of lower linkage 346 via a third pin 347b, and an upper or second portion 344b of second lateral linkage 344 is pinned to second arm 350 via a fourth pin 349b.

In the illustrated embodiment, first lateral linkage 342 and second lateral linkage 344 are mirror images of each other and are generally z-shaped, and lower linkage 346 is generally u- or c-shaped; other shapes and configurations are contemplated without departing from the scope of the present disclosure.

Figure 7:
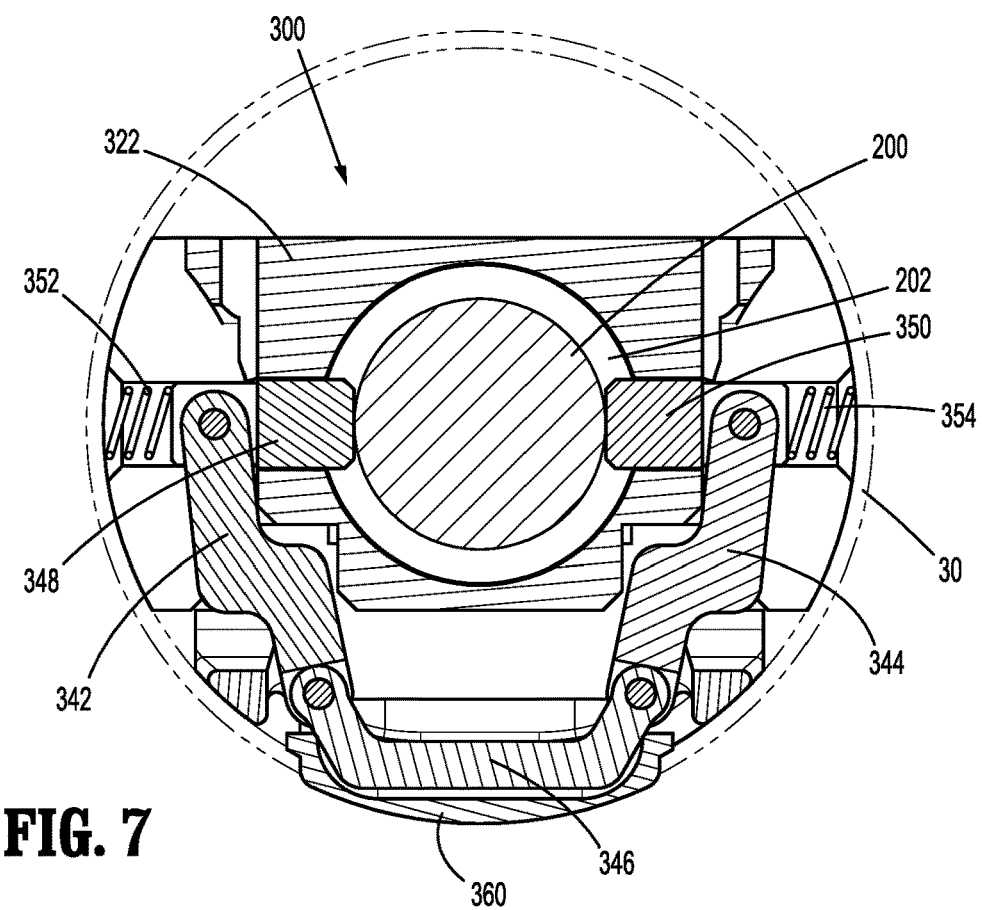
FIG. 7 is a cross-sectional view of the trocar retaining assembly, the trocar assembly and the elongated body portion taken along line 7-7 in FIG. 6.
Figure 9:
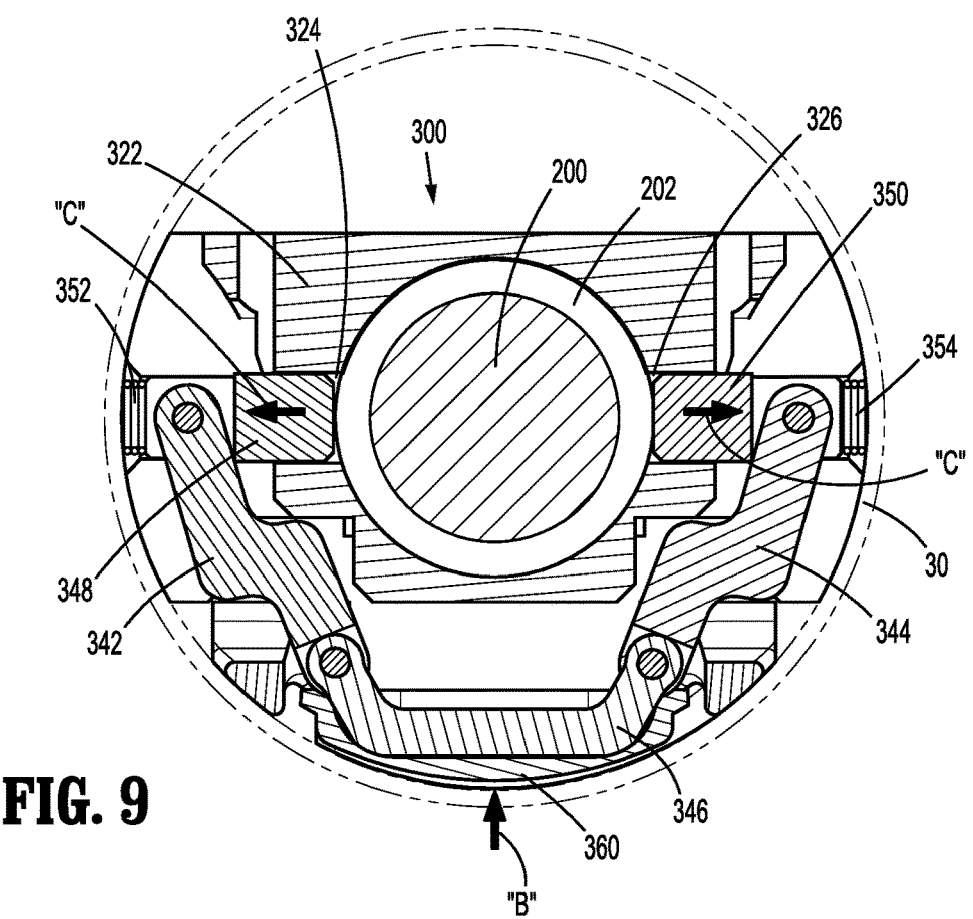
FIG. 9 is a cross-sectional view of the trocar retaining assembly, the trocar assembly and the elongated body portion taken along line 9-9 in FIG. 8.
Figure 10:
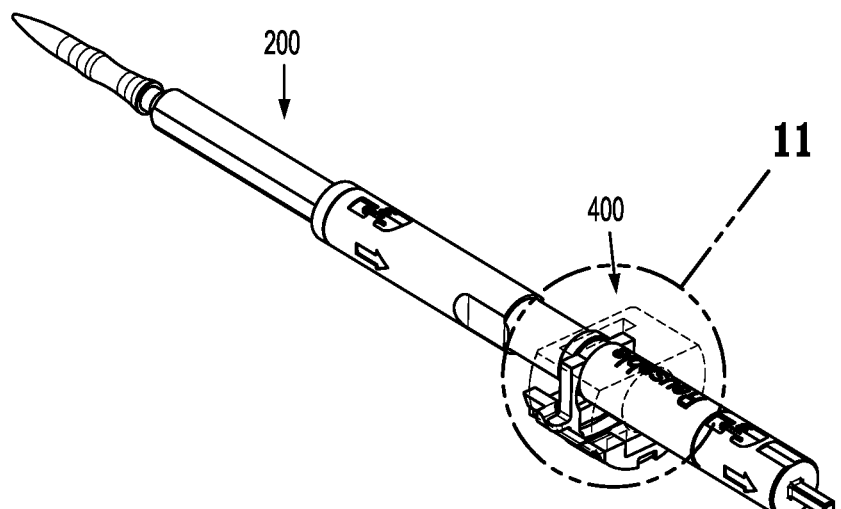
FIG. 10 is a perspective view of a second embodiment of a trocar retaining assembly engaged with a trocar assembly in accordance with an embodiment of the present disclosure.
Figure 11:
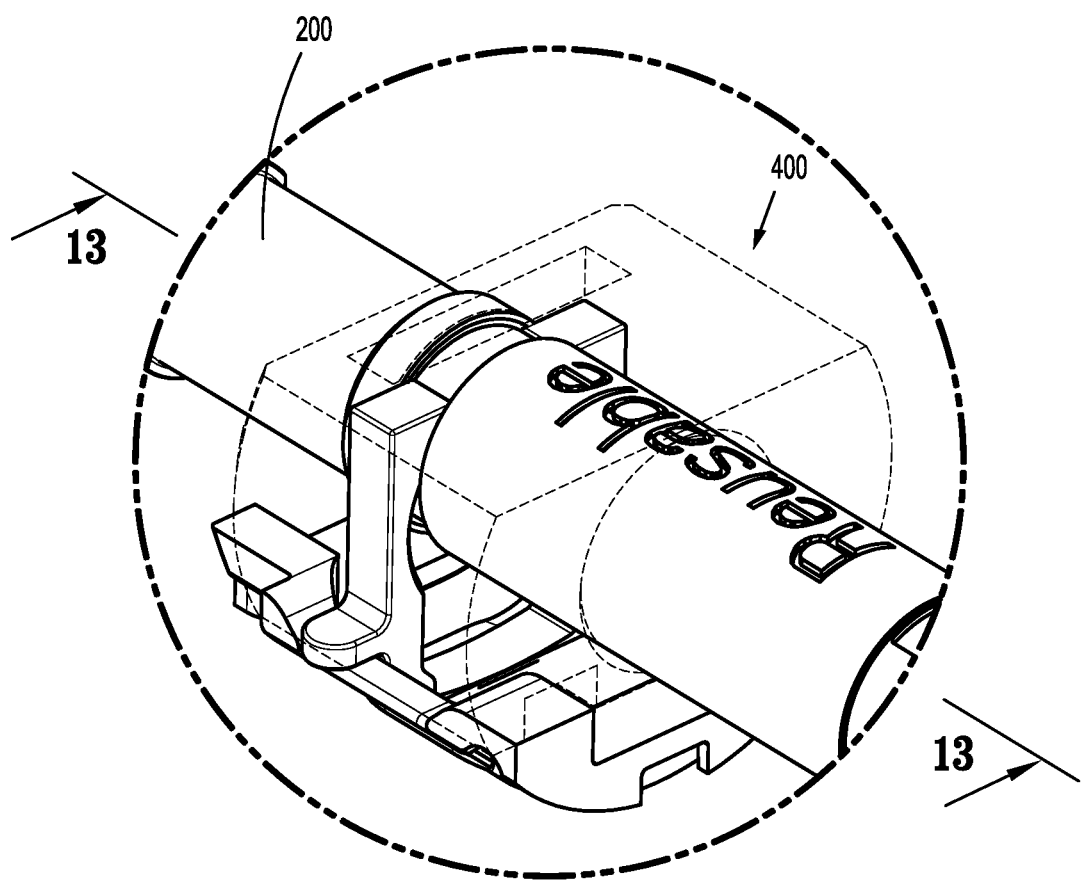
FIG. 11 is an enlarged view of the area of detail indicated in FIG. 10, with portions omitted for clarity.

As shown in FIGS. 7 and 9, at least a portion of first arm 348 is slidably positioned within a first lateral aperture 324 (FIGS. 5 and 9) of upper housing 322 of housing assembly 320, and at least a portion of second arm 350 is slidably positioned within a second lateral aperture 326 (FIG. 9) of upper housing 322 of housing assembly 320.

With continued reference to FIGS. 7 and 9, when trocar retaining assembly 300 is positioned within, or at least partially within elongated body portion 30 of circular stapler 10, first biasing member 352 is positioned between an inner wall of elongated body portion 30 and a lateral end of first arm 348, and urges first arm 348 radially inward toward and into engagement and/or contact with trocar assembly 200 (e.g., within an annular groove 202 of trocar assembly 200). Additionally, second biasing member 354 is positioned between the inner wall of elongated body portion 30 and a lateral end of second arm 350, and urges second arm 350 radially inward toward and into engagement and/or contact with trocar assembly 200 (e.g., within annular groove 202 of trocar assembly 200).

In use, first biasing member 352 and second biasing member 354 bias portions of first arm 348 and second arm 350, respectively, into annular groove 202 of trocar assembly 200, thereby preventing or hindering longitudinal movement (e.g., removal) of trocar assembly 200 relative to elongated body portion 30 of circular stapler 10.

Figure 8:
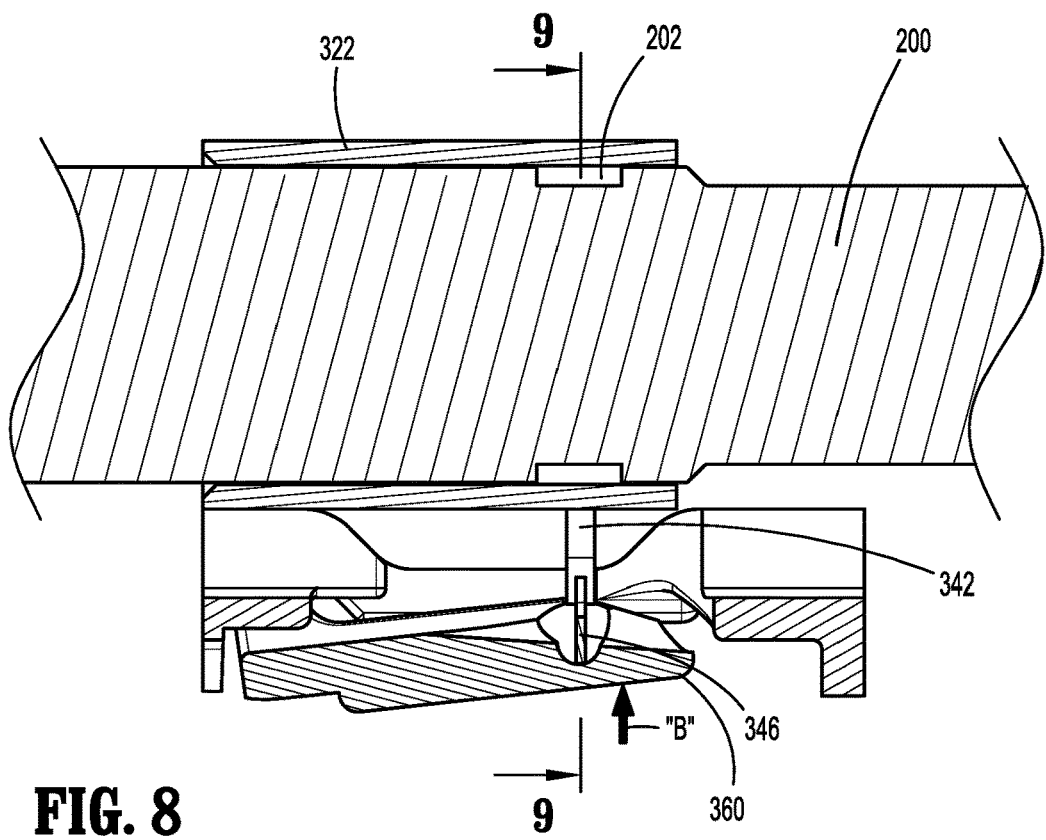
FIG. 8 is a cross-sectional view of the trocar retaining assembly of FIGS. 4 and 5 engaged with the trocar assembly of FIGS. 3 and 4, and illustrating the trocar release button in a depressed position.

To remove trocar assembly 200 from elongated body portion 30 (e.g., for cleaning), a user moves or depresses actuator 360 (or lower linkage 346 in embodiments lacking an actuator 360) toward trocar assembly 200 or longitudinal axis A-A in the general direction of arrow "B" in FIGS. 8 and 9. Elongated body portion 30 includes an opening 32 (FIGS. 2 and 3) through its wall, which is aligned with actuator 360 thereby enabling a user to access or engage lower linkage 346. As shown when comparing FIGS. 7 and 9, for instance, this movement of lower linkage 346 causes first lateral linkage 342 and second lateral linkage 344 to move radially outward in the general direction of arrows "C" in FIG. 9, against the bias of first biasing member 352 and second biasing member 354, respectively, thereby causing first arm 348 and second arm 350 to move radially outward and out of engagement with annular groove 202 of trocar assembly 200. When first arm 348 and second arm 350 are not within annular groove 202 of trocar assembly 200, trocar assembly 200 is able to be removed from elongated body portion 30 of circular stapler 10.

Referring now to FIGS. 10-16, a second embodiment of a trocar retaining assembly is shown and is referred to by reference character 400. Trocar retaining assembly 400 is configured to releasably retain trocar assembly 200 at least partially within elongated body portion 30 of circular stapler 10, and to allow trocar assembly 200 to be removed from elongated body portion 30 for cleaning and/or reuse, for example. Trocar retaining assembly 400 includes a housing assembly 420, a button assembly 440, and an actuator 480.

Figure 12:
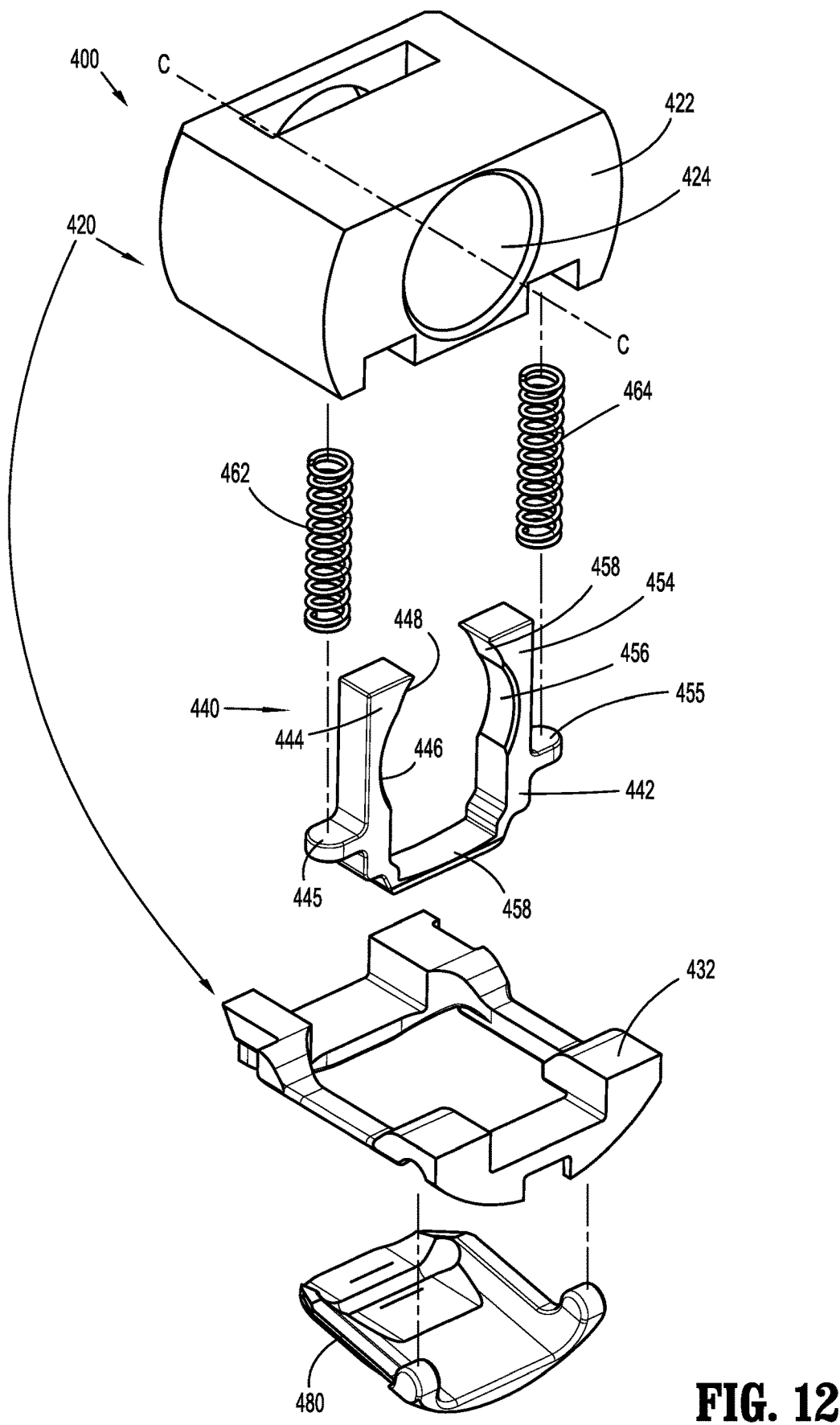
FIG. 12 is an exploded perspective view of the trocar retaining assembly of FIGS. 10 and 11.

With particular reference to FIG. 12, housing assembly 420 includes an upper housing 422 and a lower housing 432. Upper housing 422 and lower housing 432 are configured to engage each other in a snap-fit manner, for example. Upper housing 422 defines a trocar aperture 424, which defines a longitudinal axis C-C and which is configured to slidingly receive a portion of trocar assembly 200 therethrough (FIGS. 13-16). The engagement between upper housing 422 and lower housing 432 secures portions of button assembly 440 therebetween. Actuator 480 is configured to mechanically engage lower housing 432 (e.g., via snap-fit engagement).

Figure 13:
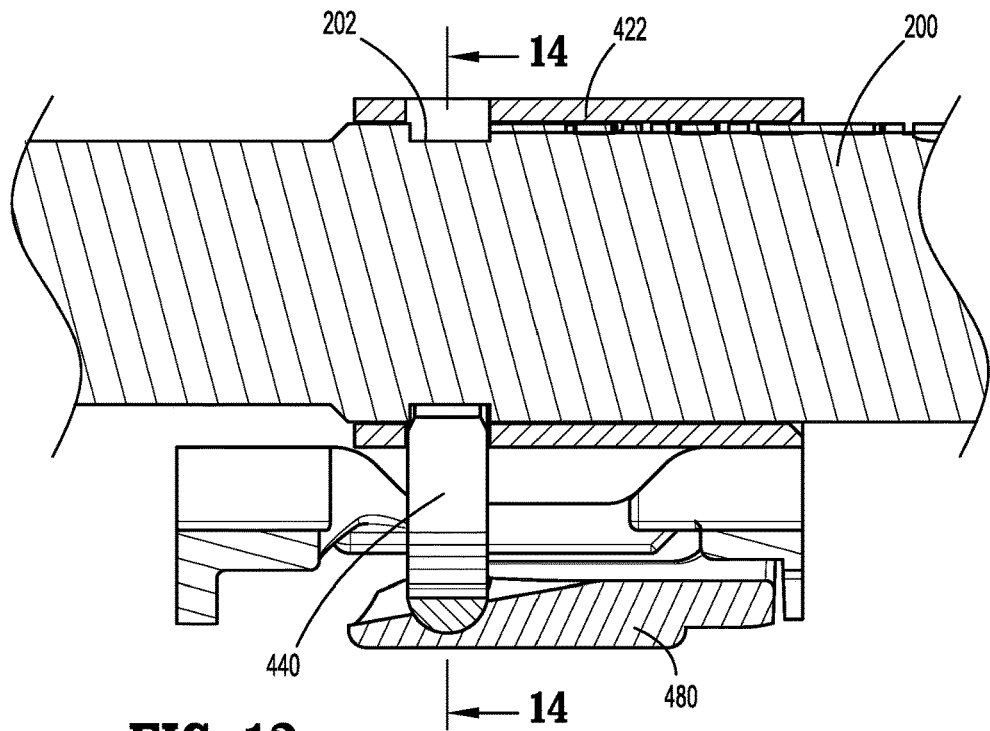
FIG. 13 is a cross-sectional view of the trocar retaining assembly and the trocar assembly taken along line 13-13 in FIG. 11, and illustrating a trocar release button in a rest position.
Figure 14:
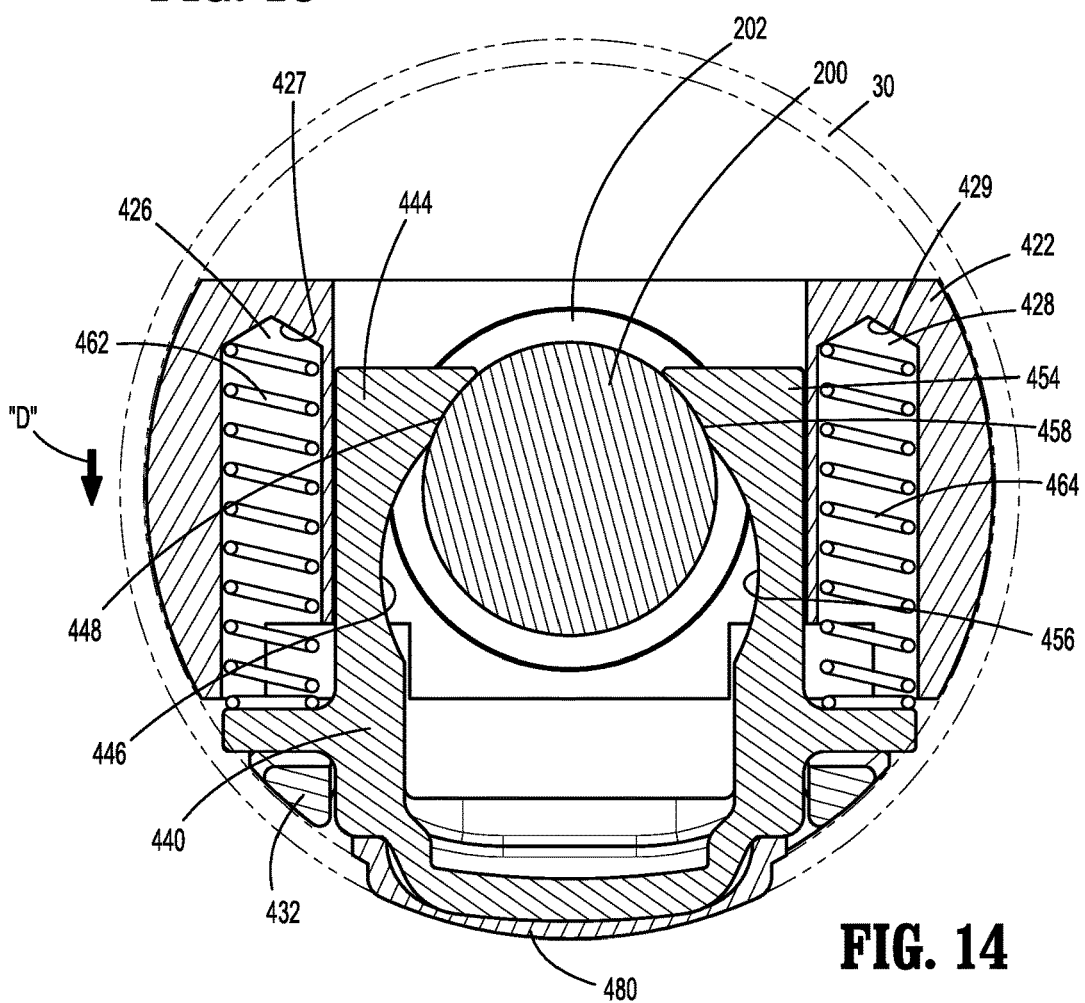
FIG. 14 is a cross-sectional view of the trocar retaining assembly, the trocar assembly and the elongated body portion taken along line 14-14 in FIG. 13.
Figure 15:
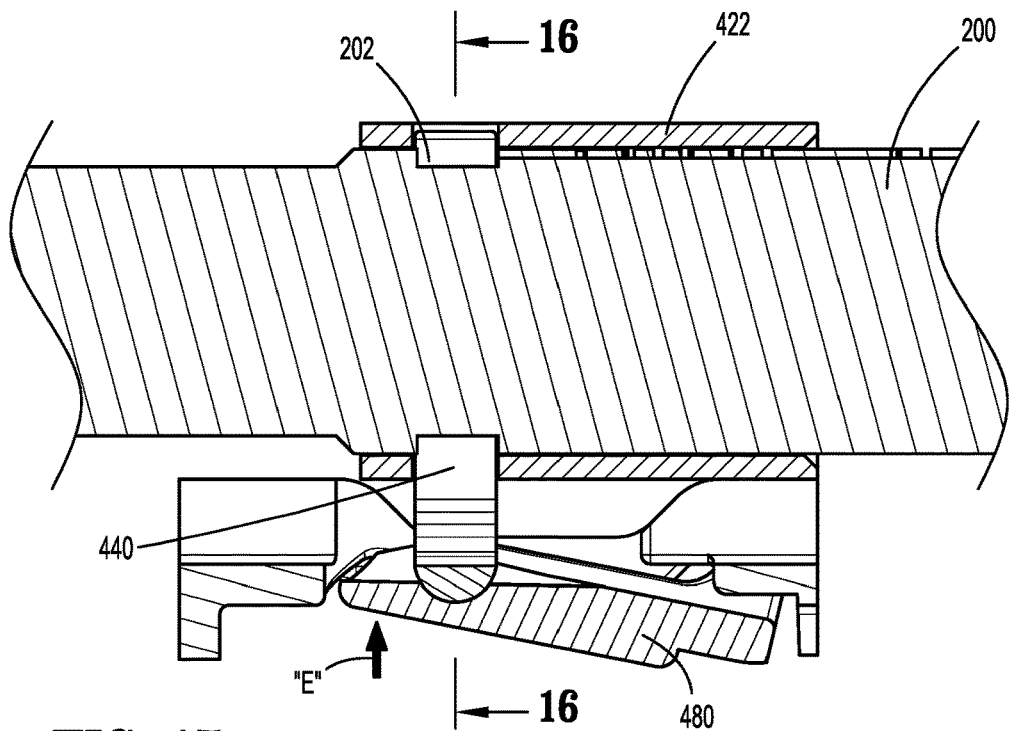
FIG. 15 is a cross-sectional view of the trocar retaining assembly of FIGS. 11 and 12 engaged with the trocar assembly of FIGS. 10 and 11, and illustrating the trocar release button in a depressed position.
Figure 16:
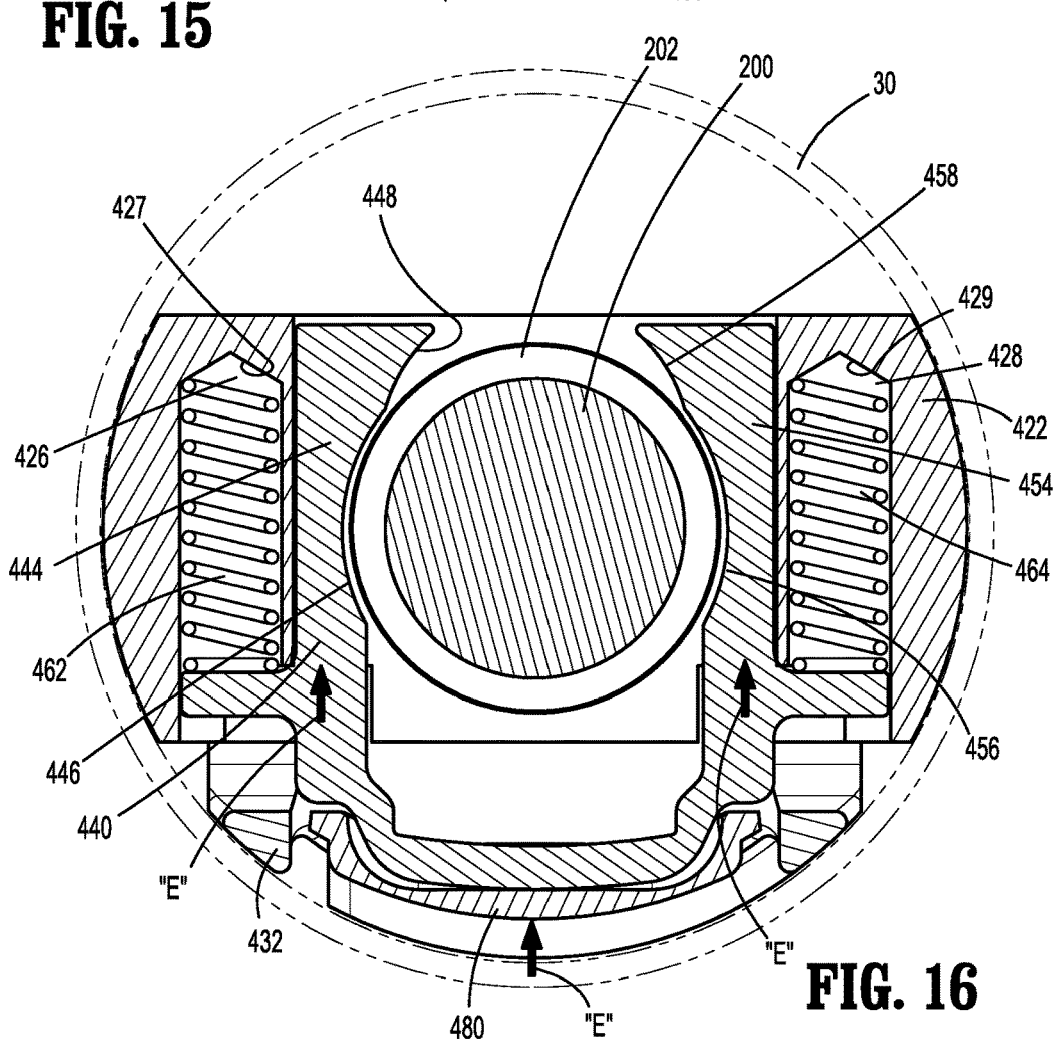
FIG. 16 is a cross-sectional view of the trocar retaining assembly, the trocar assembly and the elongated body portion taken along line 16-16 in FIG. 15.

With continued reference to FIG. 12, button assembly 440 includes a movable button 442, a first biasing member 462 and a second biasing member 464. Movable button 442 includes a first leg 444 and a second leg 454 depending from a backspan 458. First leg 444 includes a first shelf 445 extending outwardly (e.g., perpendicularly) therefrom, and second leg 454 includes a second shelf 455 extending outwardly (e.g., perpendicularly) therefrom. An inner-facing portion of first leg 444 includes a first curved part 446 including a first arc length, and a second curved part 448 having a second arc length. Similarly, an inner-facing portion of second leg 454 includes a first curved part 456 including a first arc length, and a second curved part 458 having a second arc length. The first curved part 446 of first leg 444 and the first curved part 456 of second leg 454 are configured to engage trocar assembly 200 (e.g., annular groove 202 thereof) when button assembly 440 is in a first, biased position (FIGS. 13 and 14). The second curved part 448 of first leg 444 and the second curved part 458 of second leg 454 are configured to be spaced from trocar assembly 200 when button assembly 440 is in a second, actuated position (FIGS. 15 and 16).

In the illustrated embodiment, first leg 444 and second leg 454 of movable button 442 of button assembly 440 are mirror images of each other; other shapes and configurations are contemplated without departing from the scope of the present disclosure.

With reference to FIG. 14, first biasing member 462 is positioned at least partially within a first cavity 426 of upper housing 422, and between first shelf 445 of first leg 444 and an opposing wall 427 of first cavity 426. Second biasing member 464 is positioned at least partially within a second cavity 428 of upper housing 422, and between second shelf 455 of second leg 454 and an opposing wall 429 of second cavity 428.

In use, first biasing member 462 and second biasing member 464 bias button assembly 440 in the general direction of arrow "D" (FIG. 14) into the position illustrated in FIGS. 13 and 14. Here, second curved part 448 of first leg 444 and second curved part 458 of second leg 454 are biased into annular groove 202 of trocar assembly 200, thereby preventing or hindering longitudinal movement (e.g., removal) of trocar assembly 200 relative to elongated body portion 30 of circular stapler 10.

To remove trocar assembly 200 from elongated body portion 30 (e.g., for cleaning), a user moves or depress actuator 480 (or backspan 458 of movable button 442 in embodiments lacking actuator 480) toward trocar assembly 200 or longitudinal axis A-A in the general direction of arrows "E" (FIGS. 15 and 16). Referring back to FIG. 3, opening 32 through wall of elongated body portion 30 is aligned with actuator 480 thereby enabling a user to access to actuator 480. As shown when comparing FIGS. 14 and 16, for instance, this movement of actuator 480 causes first leg 444 and second leg 454 to move away from opening 32 of elongated body portion 30 in the general direction of arrows "E" in FIG. 16, against the bias of first biasing member 462 and second biasing member 464, respectively, thereby causing first curved part 446 of first leg 444 and first curved part 456 of second leg 454 to become aligned with trocar assembly 200. With particular reference to FIG. 16, in this orientation, the second curved parts 448, 458 of first leg 444 and second leg 454, respectively, are slightly spaced from trocar assembly 200, thereby allowing trocar assembly 200 to longitudinally translate with respect to trocar retaining assembly 400, and is thus able to be removed from elongated body portion 30 of circular stapler 10.

Referring now to FIGS. 17-21, a third embodiment of a trocar retaining assembly is shown and is referred to by reference character 500. Trocar retaining assembly 500 is configured to releasably retain trocar assembly 200 at least partially within elongated body portion 30 of circular stapler 10, and to allow trocar assembly 200 to be removed from elongated body portion 30 for cleaning and/or reuse, for example. Trocar retaining assembly 500 includes a housing assembly 520, a spring assembly 540, a first pin 560 and a second pin 570.

Figure 19:
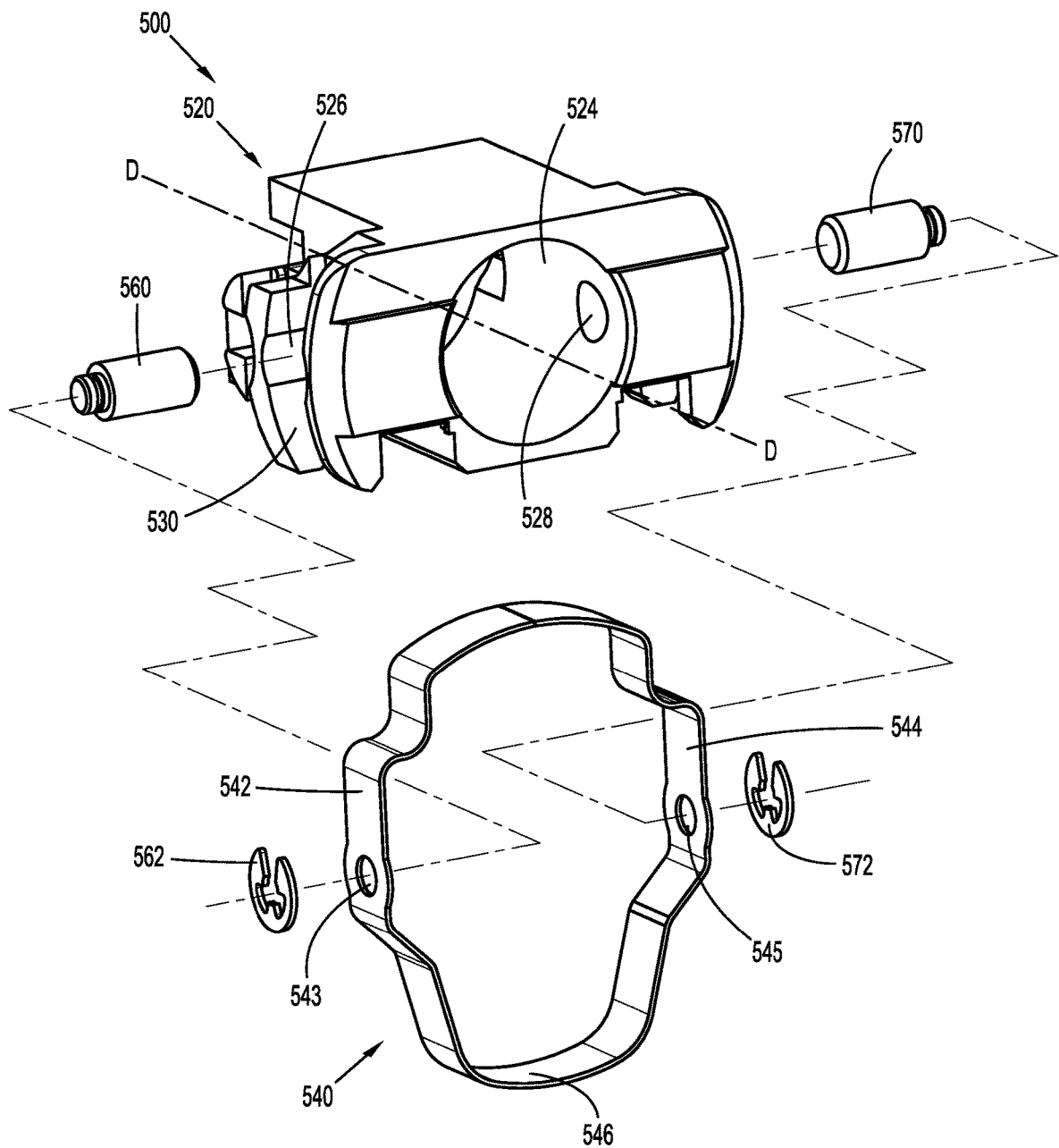
FIG. 19 is an exploded perspective view of the trocar retaining assembly of FIGS. 17 and 18.

With particular reference to FIG. 19, housing assembly 520 defines a trocar aperture 524, which defines a longitudinal axis D-D and which is configured to slidingly receive a portion of trocar assembly 200 therethrough (FIGS. 20 and 21). Housing assembly 520 also defines a first lateral cavity 526 configured for sliding reception of first pin 560, and a second lateral cavity 528 configured for sliding reception of second pin 570.

Referring now to FIGS. 18 and 19, spring assembly 540 is positioned about (e.g., forms a ring around) housing assembly 520. More particularly, a first lateral side 542 of spring assembly 540 is positioned within a first lateral channel 530 of housing assembly 520, and a second lateral side 544 of spring assembly 540 is positioned within a second lateral channel 532 of housing assembly 520.

In the illustrated embodiment, first lateral side 542 of spring assembly 540 and second lateral side 544 of spring assembly 540 are mirror images of each other; other shapes and configurations are contemplated without departing from the scope of the present disclosure.

A portion of first pin 560 is disposed within first lateral cavity 526 of housing assembly 520, and another portion of first pin 560 extends through a first opening 543 of first lateral side 542 of spring assembly 540 and into engagement with a first retainer 562. A portion of second pin 570 is disposed within second lateral cavity 528 of housing assembly 520, and another portion of second pin 570 extends through a second opening 545 of second lateral side 544 of spring assembly 540 and into engagement with a second retainer 572. First pin 560 is slidable relative to first lateral cavity 526 of housing assembly 520, and is fixed from sliding relative to first lateral side 542 of spring assembly 540 due to the engagement between first pin 560 and first retainer 562. Second pin 570 is slidable relative to second lateral cavity 528 of housing assembly 520, and is fixed from sliding relative to second lateral side 544 of spring assembly 540 due to the engagement between second pin 570 and second retainer 572.

Referring back to FIG. 3, elongated body portion 30 includes opening 32 through its wall, which is aligned with a lower portion 546 of spring assembly 540 thereby enabling a user to access to lower portion 546 of spring assembly 540 or actuator.

With reference to FIGS. 20 and 21, when trocar retaining assembly 500 is positioned within, or at least partially within elongated body portion 30 of circular stapler 10, the natural bias of spring assembly 540 urges first pin 560 and second pin 570 radially inward toward and into engagement and/or contact with trocar assembly 200 (e.g., within an annular groove 202 of trocar assembly 200) (FIG. 20), thereby preventing or hindering longitudinal movement (e.g., removal) of trocar assembly 200 relative to elongated body portion 30 of circular stapler 10.

To remove trocar assembly 200 from elongated body portion 30 (e.g., for cleaning), a user moves or depress lower portion 546 of spring assembly 540 (or an actuator engaged therewith) toward trocar assembly 200 or longitudinal axis A-A in the general direction of arrow "F" in FIG. 21. As shown when comparing FIGS. 20 and 21, for instance, this movement of lower portion 546 of spring assembly 540 causes the force applied thereto to be transferred through spring assembly 540 along the general direction of arrows "G," "H," "I," and "J" (e.g., by compressing portions of spring assembly 540) such that first lateral portion 542 and second lateral portion 544 of spring assembly 540 move radially outward in the general direction of arrows "K" and "L" (FIG. 21), respectively, against the bias of spring assembly 540, thereby causing first pin 560 and second pin 570 to move radially outward and out of engagement with annular groove 202 of trocar assembly 200. When first pin 560 and second pin 570 are not within annular groove 202 of trocar assembly 200, trocar assembly 200 is able to be removed from elongated body portion 30 of circular stapler 10.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A trocar retaining assembly configured to releasably retain a trocar assembly relative to an elongated body portion of a surgical stapling instrument, the trocar retaining assembly comprising:
a housing assembly defining a trocar aperture, the trocar aperture defining a longitudinal axis and configured to slidingly receive a portion of a trocar assembly; and
a button assembly including a first leg extending from a backspan, a portion of the first leg including a first curved part defining a first arc length and a second curved part defining a second arc length, the first leg movable relative to the housing assembly between a first position where the first curved part is coaxial with the longitudinal axis, and a second position where the second curved part is coaxial with the longitudinal axis,
wherein the trocar assembly is hindered from translating longitudinally relative to the housing assembly when the first leg is in its second position, the trocar assembly is longitudinally translatable relative to the housing assembly when the first leg is in its first position, and the second curved part of the first leg is configured to selectively contact a longitudinally-translatable portion of the trocar assembly.

2. The trocar retaining assembly according to claim 1, wherein the button assembly includes a second leg extending from the backspan, a portion of the second leg including a first curved part defining the first arc length and a second curved part defining the second arc length, the second leg movable relative to the housing assembly between a first position where the first curved part is coaxial with the longitudinal axis, and a second position where the second curved part is coaxial with the longitudinal axis.

3. The trocar retaining assembly according to claim 2, wherein moving the backspan toward the trocar aperture causes the first leg to move toward its first position.

4. The trocar retaining assembly according to claim 2, wherein the second leg is a mirror image of the first leg.

5. The trocar retaining assembly according to claim 2, wherein the second leg is immovable relative to the first leg.

6. The trocar retaining assembly according to claim 1, wherein the first leg is biased toward its second position.

7. The trocar retaining assembly according to claim 1, wherein the housing assembly defines a first cavity disposed on a first lateral side of the trocar aperture, and a second cavity disposed on a second lateral side of the trocar aperture.

8. The trocar retaining assembly according to claim 7, further comprising a first biasing member disposed at least partially within the first cavity and in contact with the first leg of the button assembly, and a second biasing member disposed at least partially within the second cavity and in contact with the second leg of the button assembly.

9. The trocar retaining assembly according to claim 8, wherein the first biasing element biases the first leg toward its second position.

10. The trocar retaining assembly according to claim 1, wherein the second curved part of the first leg is positioned farther from the backspan than the first curved part of the first leg.

11. A trocar retaining assembly configured to releasably retain a trocar assembly relative to an elongated body portion of a surgical stapling instrument, the trocar retaining assembly comprising:
a housing assembly defining a trocar aperture, the trocar aperture defining a longitudinal axis and configured to slidingly receive a portion of a trocar assembly; and
a button assembly including a first leg extending from a backspan, the first leg including a first arcuate portion and a second arcuate portion, a concave portion of the second arcuate portion defining the same radius of curvature as a longitudinally-translatable portion of the trocar assembly, the first leg movable relative to the housing assembly between a first position where the second arcuate portion is spaced a first distance from the longitudinal axis, and a second position where the second arcuate portion is spaced a second distance from the longitudinal axis, the first distance being larger than the second distance.

12. The trocar retaining assembly according to claim 11, wherein the second arcuate portion of the first leg is configured to contact the trocar assembly when the portion of the trocar assembly is within the trocar aperture and when the first leg is in its second position.

13. The trocar retaining assembly according to claim 12, wherein the second arcuate portion of the first leg is configured to be spaced apart from the trocar assembly when the portion of the trocar assembly is within the trocar aperture and when the first leg is in its first position.

14. The trocar retaining assembly according to claim 11, wherein the first leg is biased toward its second position.

15. The trocar retaining assembly according to claim 11, wherein moving the backspan toward the trocar aperture causes the first leg to move toward its first position.

16. The trocar retaining assembly according to claim 11, wherein the second arcuate portion of the first leg is positioned farther from the backspan than the first arcuate portion of the first leg.

17. The trocar retaining assembly according to claim 11, wherein the button assembly includes a second leg extending from the backspan, the second leg including a first arcuate portion and a second arcuate portion.

18. The trocar retaining assembly according to claim 17, wherein the second leg is a mirror image of the first leg.

19. The trocar retaining assembly according to claim 17, wherein the second leg is immovable relative to the first leg.

20. The trocar retaining assembly according to claim 11, wherein the backspan of the button is biased away from the longitudinal axis.

* * * * *